(12) United States Patent
Lu

(10) Patent No.: US 11,826,355 B1
(45) Date of Patent: Nov. 28, 2023

(54) ASPIRIN-MIMETIC ANTIOXIDANTS FOR TREATMENT OF AGE-RELATED CATARACT

(71) Applicant: Yansong Lu, Edison, NJ (US)

(72) Inventor: Yansong Lu, Edison, NJ (US)

(*) Notice: Subject to any disclaimer, the term of this patent is extended or adjusted under 35 U.S.C. 154(b) by 0 days.

(21) Appl. No.: 17/817,812

(22) Filed: Aug. 5, 2022

(30) Foreign Application Priority Data

Jul. 5, 2022 (CN) .......................... 202210791555.7

(51) Int. Cl.
| | | |
|---|---|---|
| *A61K 31/4406* | (2006.01) | |
| *A61P 27/12* | (2006.01) | |
| *A61K 31/25* | (2006.01) | |
| *A61K 9/00* | (2006.01) | |
| *A61K 31/265* | (2006.01) | |

(52) U.S. Cl.
CPC ........ *A61K 31/4406* (2013.01); *A61K 9/0048* (2013.01); *A61K 31/265* (2013.01); *A61P 27/12* (2018.01)

(58) Field of Classification Search
CPC .............. A61K 31/4406; A61K 31/265; A61K 9/0048; A61P 27/12
See application file for complete search history.

(56) References Cited

U.S. PATENT DOCUMENTS 9,994,519 B2 * 6/2018 Lu .......................... C07D 487/04

FOREIGN PATENT DOCUMENTS

WO    2015053797 A2    4/2015

OTHER PUBLICATIONS

Carey et al., "In vivo inhibition of 1-buthionine-(S,R)-sulfoximine-induced cataracts by a novel antioxidant, N-acetylcysteine amide," Free Radical Biology & Medicine (2010); 50(6): pp. 722-729.
Beltz et al., "A Dual Therapeutic Approach for the Reversal of Cataracts," Free Radical Biology and Medicine (2016); 100: p. 156.

* cited by examiner

*Primary Examiner* — Timothy R Rozof
(74) *Attorney, Agent, or Firm* — Fox Rothschild LLP

(57) ABSTRACT

Pharmaceutical compositions comprising antioxidant drugs in the form of eye drops for treatment of age-related cataract, and methods thereof, are disclosed.

11 Claims, 1 Drawing Sheet

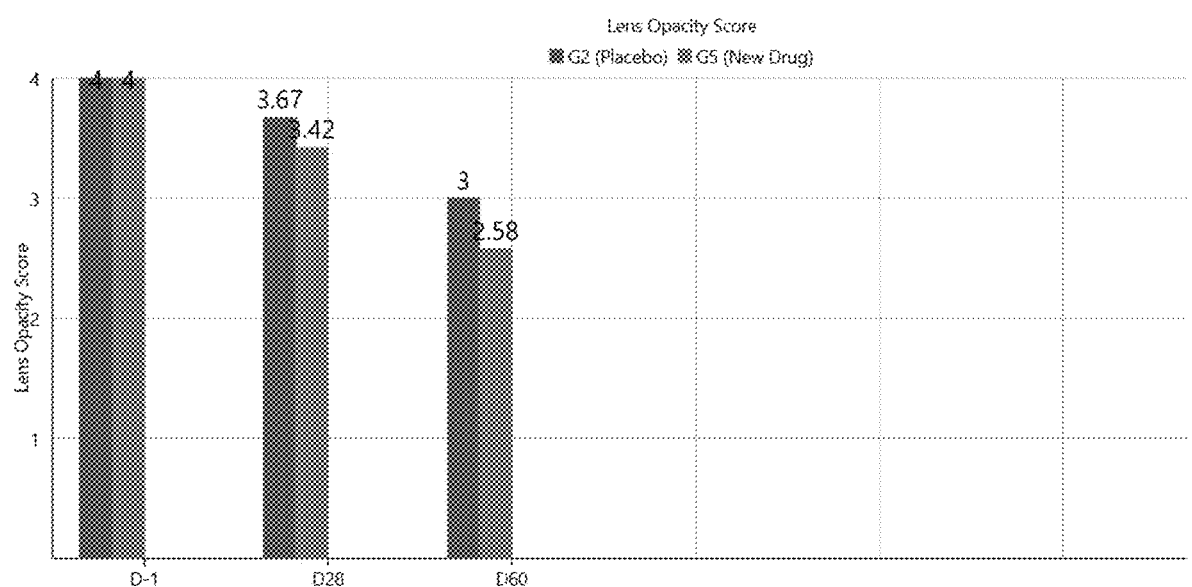

ASPIRIN-MIMETIC ANTIOXIDANTS FOR TREATMENT OF AGE-RELATED CATARACT

CROSS-REFERENCE TO RELATED APPLICATION

This application claims priority under 35 U.S.C. § 119(a) to Chinese Patent Application No. 202210791555.7, filed on Jul. 5, 2022, with the China National Intellectual Property Administration, the disclosure of which is incorporated herein by reference in its entirety.

FIELD OF THE DISCLOSURE

This disclosure relates to novel antioxidant compounds useful as therapeutic agents, in the form of eye drops for intervention of age-related cataract.

BACKGROUND OF THE DISCLOSURE

The pathogenesis and pathology of lots of major diseases remain elusive. Free radicals have been implicated in the etiology of many major diseases; therefore, antioxidants that can combat free radicals have drawn significant attention in the past decades. However, there are still very few antioxidant drugs approved for treatment of major diseases.

Numerous clinical studies have been carried out on naturally occurring antioxidants including resveratrol, vitamin A, vitamin C, vitamin E, beta-carotene, flavonoids, curcumin, and so forth, in intervention of a variety of diseases, such as neurodegenerative diseases, cancers, diabetes, inflammation, atherosclerosis, aging, etc. However, no established benefits, marginal benefits or controversial results have been obtained. In some randomized controlled clinical trials, vitamin A, vitamin E, or beta-carotene has caused higher adverse effects, such as higher mortality or higher risk of certain cancers. For example, these adverse results were observed in RCTs on prevention of cancers, such as Olli P. Heinonen and Demetrius Albanes, *N. Engl. J. Med.* 330(15), 1029-1035 (1994) ("1994 ATBC RCT"), Gilbert S. Omenn, et al., *N. Engl. J Med.* 334(18), 1150-1155 (1996) ("1996 CARET RCT"), Scott M. Lippman and Eric A. Klein, *JAMA,* 301(1), 39-51 (2009) ("2008 SELECT RCT") (Table I).

TABLE I

Three Randomized Clinical Trials on Antioxidants

| Name of Clinical Trials | Subject Antioxidants | Adverse Effects |
| --- | --- | --- |
| 1994 ATBC RCT | Beta-carotene only | 18% more lung cancer |
| 1996 CARET RCT | Beta-carotene and Vit A | 28% more lung cancer |
| 2008 SELECT RCT | Vitamin E | 17% more prostate cancer |

There is no plausible explanation on these adverse results, and there has been no critical breakthrough for antioxidant drugs thereof. There is a truly need for breakthrough. Antioxidant drug Edaravone has been approved in Japan, China, and USA, for either acute ischemia stroke (AIS) and/or ALS. Edaravone is a compound identified in 1950's, but it doesn't solve the issue of antioxidants, and it shows only marginal efficacy (5%).

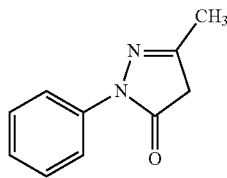

Edaravone

Aspirin is perhaps the most popular drug in the world. Like other drugs, aspirin has its side effects. The adverse effects of long-term daily usage of aspirin include stomach ulcers, gastrointestinal bleeding, and so forth.

Aspirin is used for many indications. Some aspirin analogues have been reported, such as Thioaspirin and Thiomersal. Thiomersal is toxic due to its ethyl mercury part, which is approved only for external use as antiseptic/antifungal agent, such as preservative, nasal sprays, eye drops, etc. No preclinical study on thioaspirin has been reported. Both thioaspirin and thiomersal yield thiosalicylic acid in vivo. Thiosalicylic acid is a thiophenol-based antioxidant.

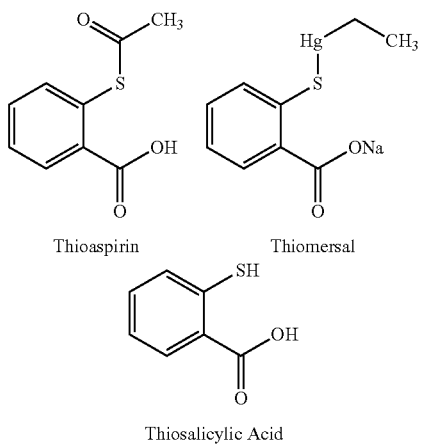

Thioaspirin   Thiomersal

Thiosalicylic Acid

Cataract is an eye disease characterized by that the lens of eyes becomes opaque, causing vision issues. The pathogenesis of cataract is not clear, and there is currently no approved medicine for treatment of cataract. Although cataract could be treated by surgery, the surgery therapy has its own drawbacks and limitations. For example, the costs of the surgery are often high, $10k to $20k per eye surgery; patients with high blood pressure, high eye pressure, diabetic conditions, and low platelet conditions may not be suitable for having cataract surgery; and some patients may be reluctant to take any eye surgery for assorted reasons. In addition, some eye drops are always needed for post-surgery use, such as anti-infection, dry eye syndrome, and so on.

Therefore, effective eye drop medication for cataract is highly desirable but remains unmet medical needs.

SUMMARY OF THE DISCLOSURE

The present disclosure aims to meet the foregoing unmet medical needs by providing eye drops of novel antioxidants for treatment of cataracts. The preliminary data has demonstrated that the eye drops can gradually reverse cataract in rat model. The eye drops could also serve as veterinary medicine for pets.

In one aspect, the present disclosure provides compounds of formula (I):

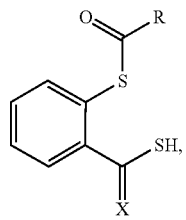

wherein X is O or S, and R is alkyl or heteroaryl.

In another aspect, this disclosure provides an eye drops solution comprising a compound of formula (I), in any embodiment disclosed, and a pharmaceutically acceptable carrier, and optionally one or more pharmaceutical excipients.

In another aspect, the present disclosure provides a method of treating an age-related cataract in an eye of a subject, comprising administering to the eye of the subject a therapeutically effective amount of the eye drops solution described in any embodiment disclosed.

Other aspects or advantages of the present invention will be better appreciated in view of the following detailed description, drawing, Examples, and claims.

BRIEF DESCRIPTION OF THE DRAWING

FIG. 1 illustrates the Lens Opacity Score in the rat model with the comparison of antioxidant drugs with the placebo.

DETAILED DESCRIPTION OF THE DISCLOSURE

The present disclosure provides novel compounds capable of terminating free radical chain reactions, i.e., serving as free radical scavengers and/or antioxidants, useful as therapeutic agents for treatment of diseases and conditions related to reactive oxygen species (ROS) and/or reactive nitrogen species (RNS).

In one aspect, the present disclosure provides compounds of formula (I):

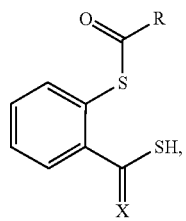

wherein X is O or S, and R is alkyl or heteroaryl.

In one embodiment, X is O.

In another embodiment, X is S.

In another embodiment, R is $C_{1-6}$ alkyl, preferably methyl or ethyl.

In another embodiment, R is a 5 to 6-membered heteroaryl, preferably pyridinyl.

In another embodiment, the compound of formula (I) is selected from:

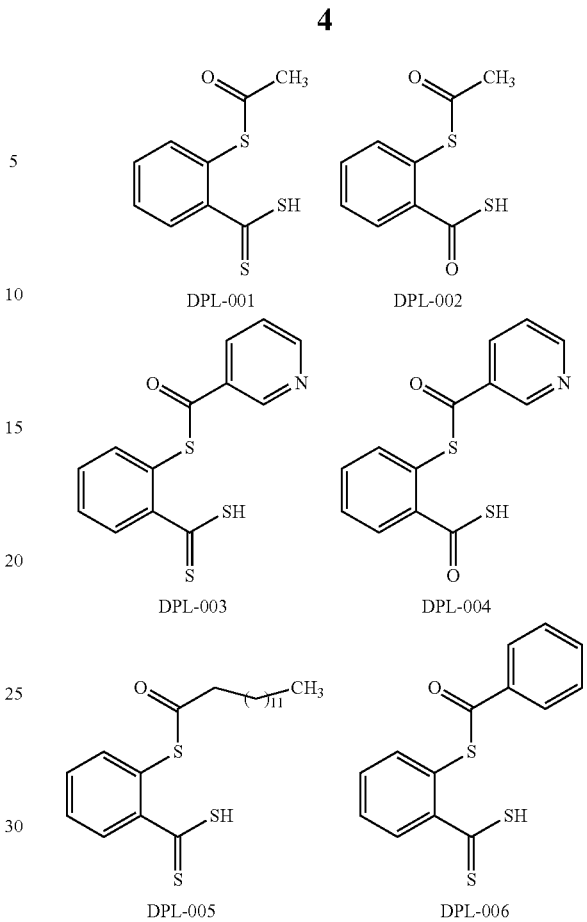

or a pharmaceutically acceptable salt thereof.

In another aspect, this disclosure provides an eye drops solution comprising a compound of formula (I) as defined above, and a pharmaceutically acceptable carrier, and optionally one or more pharmaceutical excipients.

In one embodiment of this aspect, the pharmaceutically acceptable carrier is water, and the eye drops solution further comprises a pharmaceutical excipient selected from sodium chloride, potassium chloride, boric acid, sodium borate, benzalkonium chloride, glycol, glycerin, polysorbate, carboxy methylcellulose sodium, and combinations thereof.

In one embodiment of this aspect, the concentration of the API in the eye drops solution is in a range from 0.01 mg/mL to 0.05 mg/mL.

In one embodiment of this aspect, the concentration of the API is in a range from 0.018 mg/mL to 0.036 mg/mL.

In one embodiment of this aspect, the eye drops solution has a pH in the range from 5.5 to 8.5, inclusive.

In one embodiment of this aspect, the pH of the eye drops solution is adjusted using an acid selected from hydrochloric acid, sulfuric acid, phosphoric acid, acetic acid, and combinations thereof.

In another aspect, the present disclosure provides a method of treating an age-related cataract in an eye of a subject, comprising administering to the eye of the subject a therapeutically effective amount of the eye drops solution described in any embodiment disclosed herein.

In one embodiment of this aspect, the dose range of API in the eye drops solution administered to the subject is from 10 μL to 120 μL each time, or from 0.00073 mg/kg body weight to 0.015 mg/kg body weight, or from 2.5 nmol/kg body weight to 50 nmol/kg body weight.

In one embodiment of this aspect, the eye drops solution is administered to the subject in a frequency from one time daily to five times daily.

In one embodiment, the subject is a human.

In some embodiments, the subject is a mammalian animal selected from dogs (canine), cats, rabbits, horses, ox, hamster.

So far, all known antioxidants used in preclinical and clinical studies are not good terminators of free radicals. When those antioxidants quench the primary free radicals, they themselves become new free radicals, called secondary For example, vitamin E is a strong antioxidant. However, when it quenches a free radical, it becomes a free radical itself (Scheme II), called the secondary free radical in the propagation process. The free radical form of vitamin E is a pro-oxidant, as it can still oxidize some other molecules by taking in an electron or hydrogen radical. Thus, the free radical form of vitamin E can still harm, especially in the presence of some metal cation (Fe, Cu, etc.) as the catalyst for electron transfer. Therefore, vitamin E is not a good scavenger of free radicals in this regard. The same conclusion can be drawn for various other known antioxidants.

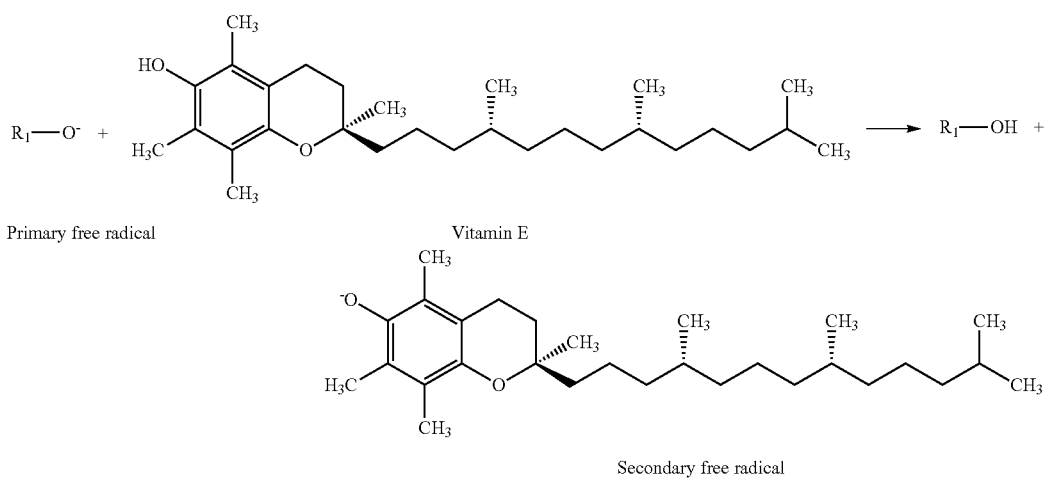

Scheme II. Alpha-Tocopherol (α-Vitamin E) Quenches A Free Radical free radicals. The secondary free radicals are less reactive compared to the primary free radicals (Scheme I). With a lower reactivity, the secondary free radicals can live longer and thus can travel a longer distance within cell/biological system compared to the corresponding primary free radicals. Based on the molecular structures of antioxidants, some secondary free radicals derived from the antioxidants, though less reactive, could reach some pivotal parts and harm DNA, lipids, and proteins via free radical oxidation. There are two explanations. First, although they are less reactive compared to the primary free radicals, the secondary free radicals are still strong enough to directly oxidize some vulnerable DNA, lipids, and proteins, etc. Second, the secondary free radicals may be too weak to directly oxidize biomolecules such as DNA, lipids, and proteins, but with some metal cation (Fe, Cu, etc.) present as the catalyst for electron transfer in vivo, they can readily oxidize some DNA, lipids, and proteins, etc.

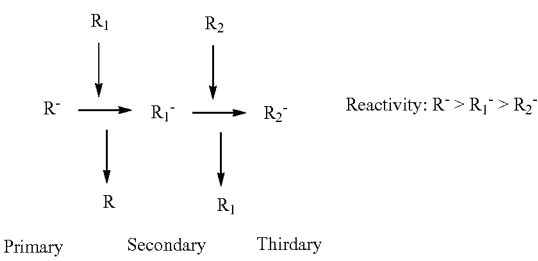

Scheme I. Propagation of Free Radicals

Those RCT data with higher incidence of some certain cancers (Table I) can be well explained now as elaboration above. On the other hand, those clinical trials can verify that the hypothesis that free radicals can cause cancers is true.

Free radical scavengers as antioxidant drugs would work. The key is to effectively terminate free radicals, to avoid the lengthy propagation of free radicals and to reduce the life expectancy of free radicals in vivo. This logic prompts innovative designs of novel aspirin-mimics in this invention. Preclinical efficacy tests on new drugs of this disclosure have showed unprecedented results, such as reversing cataract in the rat model, and suppressing the release of various cytokines on cell-based assay in anti-inflammation.

The chemical activity of free radicals can usually be completely quenched via termination. Termination of free radicals is a key concept in the working mechanisms of the novel aspirin-mimetics in this disclosure. A simple and effective method to terminate free radicals is to let one free radical react with another free radical to form a coupling compound (Scheme III). Disulfide has the highest bond energy among all interested functional groups (N-N, O-O, S-S, Se-Se) and thiol is hence one of the most powerful scavengers of free radicals among them. See, e.g., U.S. Pat. No. 9,994,519, which is hereby incorporated by reference in its entirety for all purposes.

It is well known that the antioxidant strength of thiophenol is much stronger than that of alkyl thiol like cysteine and ALA (alpha lipoic acid). Thus, thiophenol is the focus of designing novel antioxidants in this invention. Based on chemical kinetics, a dithiol-containing molecule can form a 5-membered ring (intramolecular disulfide) faster than to form an intermolecular disulfide. A disulfide formed in a 5-membered ring is also stabler than that formed in a chain. Plus, a 5-membered ring disulfide is formed with much more favored bond angles than that of ALA. Thus, the novel aspirin-mimetics in this disclosure are much better free radical scavengers than ALA.

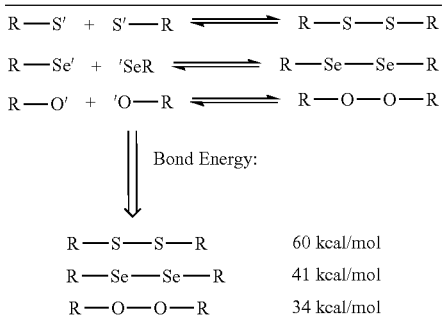

Scheme III. Termination of Free Radicals by Forming A Coupling Compound

Thio-aspirin-mimetics can efficiently terminate free radicals. The mechanism of how they effectively terminate free radicals is illustrated in Scheme IV.

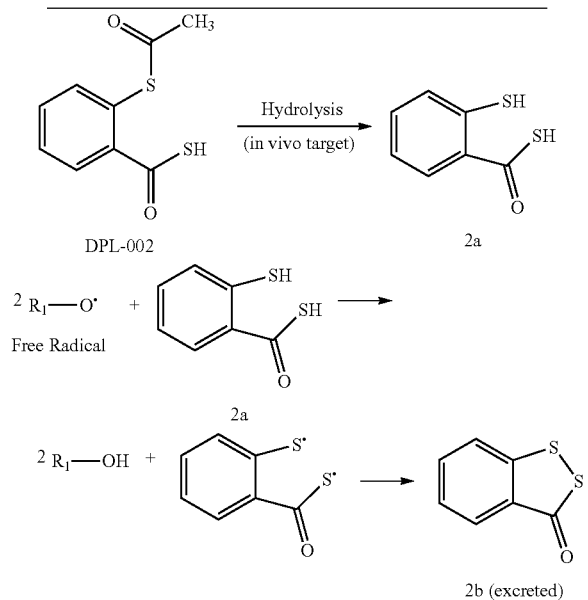

Scheme IV. Proposed Mechanism of How New Drug Terminates Free Radicals

The "druggability" of aspirin is utilized in the design of novel antioxidants in this invention. To inherit the "druggability" from aspirin, the novel antioxidants will keep the essential skeleton of aspirin molecule, but with sulfur atom to replace oxygen atom in a pair of key functional groups. In the periodic table of the elements, sulfur and oxygen are in the same "oxygen group" and are of similar properties. The replacement of oxygen with sulfur will avoid any "abrupt change" in molecular structure and the novel antioxidants thus constructed would still keep the "druggability" of aspirin. In addition, the replacement of oxygen with sulfur will enable the new molecules to be the strongest possible scavenger of free radicals, as discussed above. Plus, it will enable the new molecules to participate in "thiol-disulfide exchange" (Scheme V) and could reverse some miss-folded proteins caused by aberrant disulfide crosslinking. Based on SHAB, the replacement of oxygen with sulfur will enable the new molecules to form a stronger chelate with heavy metals (Scheme VI), which is because sulfide or thiolate is a softer base and has higher affinity to heavy metal cations (soft acids) like mercury, cadmium, lead, iron, copper, etc. Hence, the novel aspirin-mimetics in this project could efficiently remove heavy metals out of the body. The chelation power is subtle, as too weak like aspirin or too strong like EDTA has proven no good. The active ingredients of the novel aspirin-mimetics, like 2a (Scheme VI), may fit in as a perfect one.

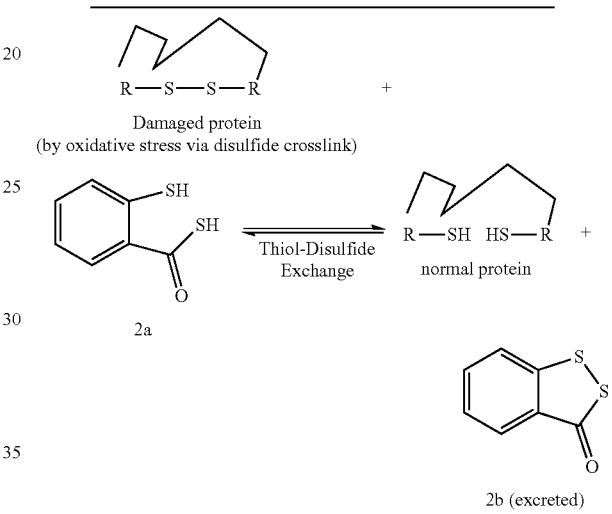

Scheme V. New Drugs Could Reverse Miss-Folded Proteins

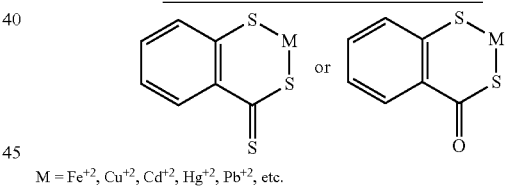

Scheme VI. Novel Drugs Can Selectively Form Stable Chelate with Heavy Metals $M = Fe^{+2}, Cu^{+2}, Cd^{+2}, Hg^{+2}, Pb^{+2}$, etc.

Antioxidant "drugs" in this invention should be in their "reduced forms". The disulfides are "oxidized form" that is not active and has no more capability of quenching free radicals. Thiol and thiophenol are the "reduced forms" of antioxidants, but they are unstable for storage because they are prone to air-oxidation. Hence, thiophenol group in this invention must be chemically protected by other functional groups. At this point, the protected one is a prodrug that can release the drug as active "reduced form" in vivo where the protection group is chemically disconnected. The protection groups selected in this invention also act as penetration enhancer, efficacy enhancer, selectivity enhancer, or a combination among them. In addition, the protection groups must have no toxicity issue.

The novel aspirin-mimetics in this invention are summarized in several models of molecular structure. Compounds DPL-001 and DPL-002 are the simplest forms of novel aspirin-mimetics in this invention. Compound 1a, the mimetic of salicylic acid, would be the active form of compound DPL-001 as free radical scavenger in vivo. Compound 2a, the mimetic of salicylic acid, would be the active form of compound DPL-002 as free radical scavenger in vivo. Compounds 1b and 2b are known, but chemically prepared via different approaches. Aspirin-mimetics in this disclosure are expected being hydrolyzed in vivo, giving compound 2a or 1a.

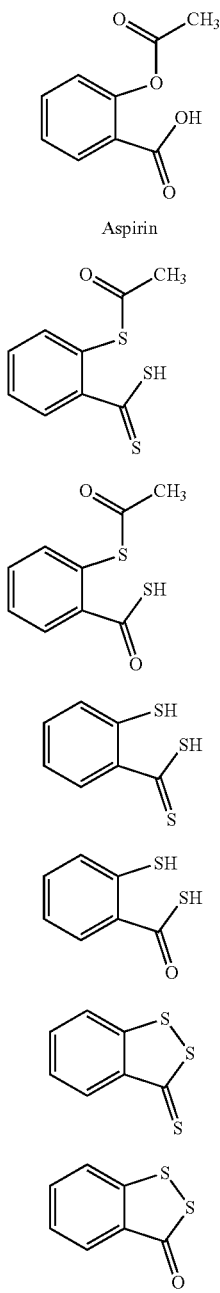

The mechanism of how a typical novel aspirin-mimetic works is proposed in Scheme IV and Scheme VII. The compound DPL-004 is delivered to the target cell such as neuron, where it is hydrolyzed to 2a. Compound 2a can efficiently terminate two free radicals in vivo. Thus, the dose of the new drugs can be halved in this regard and so does the cost of the new drugs. More importantly, this effective termination of free radicals would minimize any harm from the primary free radicals and the secondary free radicals so forth yielded in the propagation chain down the track.

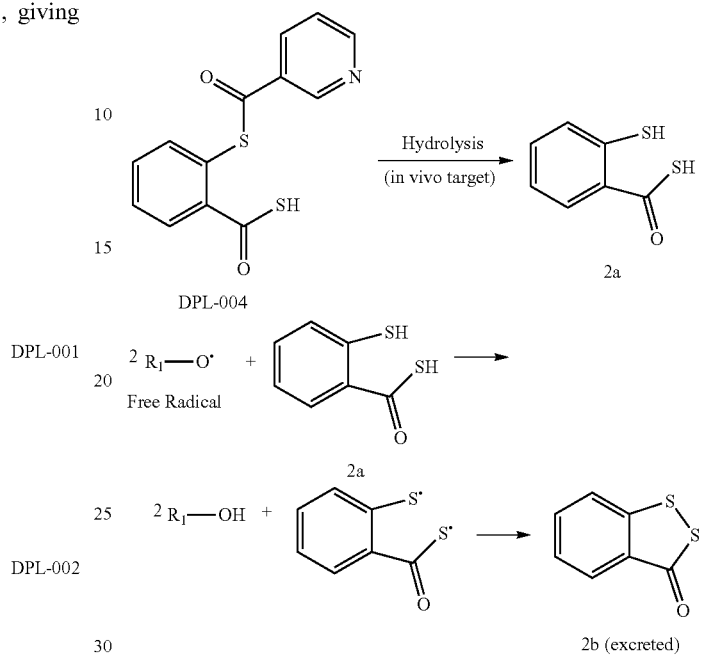

As a summary, each novel molecule in this invention consists of at least a pair of two functional groups. When oxidized, the configuration allows it to form a 5-membered ring via an intramolecular disulfide bond. The pair of functional groups consists of one thiol (—SH); and one carbodithioic acid (—CSSH), or one carbothioic acid (—COSH). Each of the pair of functional groups is covalently single-bonded with a carbon atom located on aromatic ring, or on substituted aromatic ring. The aromatic ring can be either regular aromatic ring or aromatic heterocyclic ring, with any combinations among them.

Each of the pair of functional groups can be covalently single-bonded with other functional groups selected from acetyl (—Ac), amino acid residue, vitamin B's residue, choline, dopamine, carbohydrate, nucleic base, citric acid, succinic acid, heterocycles, etc. These functional groups would act as protection group, penetration enhancer, efficacy enhancer, selectivity enhancer, or a combination among them.

As free radical is one of the possible key causes of many major diseases, it is plausible to find an antioxidant drug that can scavenge free radicals and show efficacy to many diseases like Alzheimer's disease (AD), Parkinson's disease (PD), Huntington's disease (HD), amyotrophic lateral sclerosis (ALS), diabetes, cancers, atherosclerosis, cardiovascular disease, renal disease, hypertension, hyperlipidemia, rheumatoid arthritis, lupus, multiple sclerosis (MS), gout, inflammation, pain, acne, aging, stroke, depression, cataract, glaucoma, age-related macular degeneration and HIV, and so forth. The novel antioxidants in this invention could bring answer to major diseases like cataract.

The lens proteins in eyes are transparent in normal array. Age-related cataract is opaque of the lens, wherein the lens proteins are in disarray. Although the pathogenesis of cataract is not fully elucidated, many factors associated with high incidence of cataract, like excessive exposure to heat, cosmic radiation, nuclear radiation, UV light, smoking, alcoholic, steroid, and so forth, can also help generate free radicals. When oxidized by free radicals, the primary structure of the lens proteins would be altered, and thus lead to the advanced structure change of the lens proteins, causing disarray of the lens proteins, and yielding opacity of the lens. Thus, a good scavenger of free radicals would intervene cataract as a rational design. Currently, there is no medication available to cure or prevent cataract. Surgical removal of opaque lens and implanting artificial lens is the only therapy for cataract patients. Eye drops with the novel antioxidants herein would effectively intervene cataract and offer a better option for cataract patients.

The following non-limiting examples will further illustrate certain aspects of the invention disclosed.

EXAMPLES

Chemical Synthesis of the Aspirin-Mimetics

According to the procedure reported in *J. Am. Chem. Soc.*, 1989. 111, 654-658, lithiation of thiophenol gave ortho-directed lithiation intermediate, a di-lithium salt species. That di-lithium salt species was allowed to react with carbon disulfide, followed by acetylation (via acetic anhydride), to afford compound 1 (DPL-001) in a good yield (Scheme VIII). Similarly, the di-lithium salt species can react with carbonyl sulfide, followed by acetylation (via acetic anhydride), to afford compound 2 (DPL-002) (Scheme VIII). Other new compounds were obtained when corresponding acylation reagents were applied.

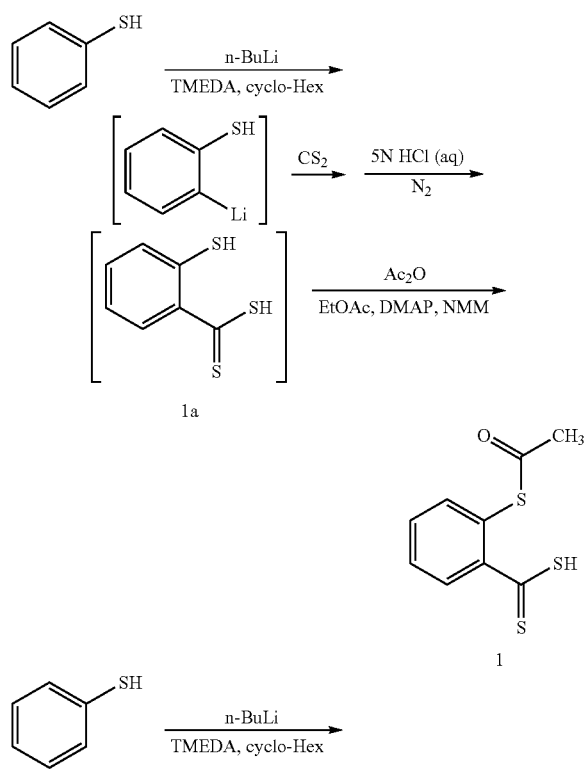

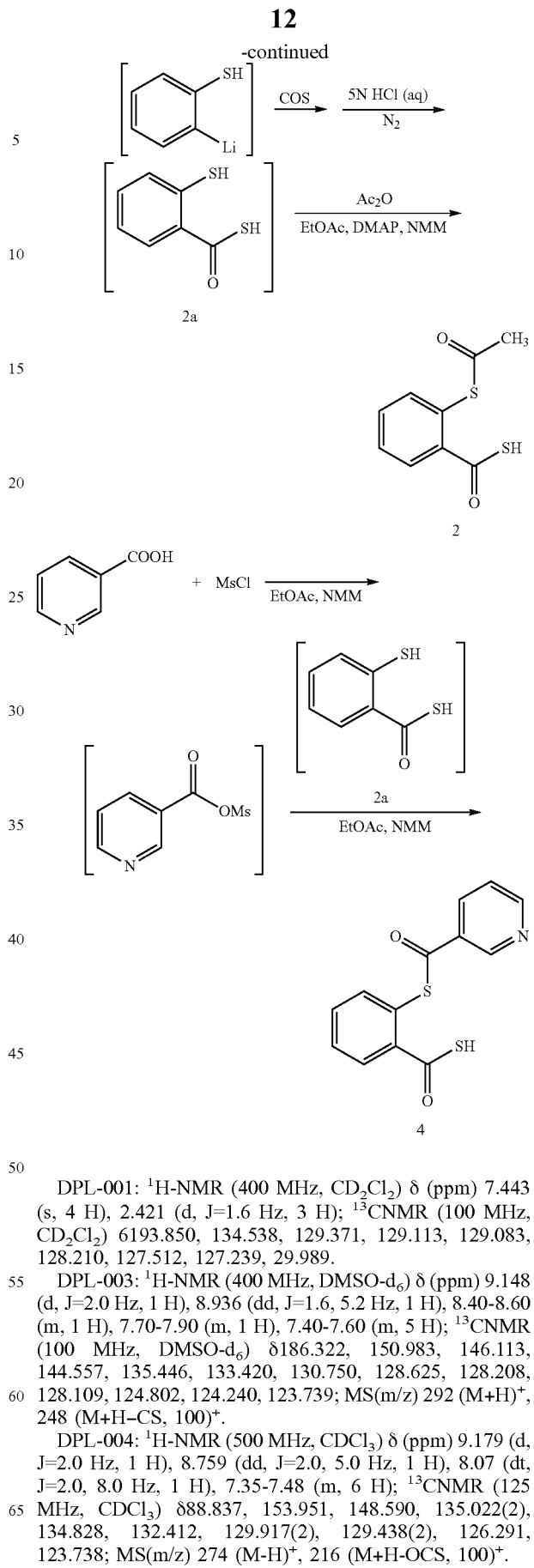

DPL-001: $^{1}$H-NMR (400 MHz, CD$_2$Cl$_2$) δ (ppm) 7.443 (s, 4 H), 2.421 (d, J=1.6 Hz, 3 H); $^{13}$CNMR (100 MHz, CD$_2$Cl$_2$) δ193.850, 134.538, 129.371, 129.113, 129.083, 128.210, 127.512, 127.239, 29.989.

DPL-003: $^{1}$H-NMR (400 MHz, DMSO-d$_6$) δ (ppm) 9.148 (d, J=2.0 Hz, 1 H), 8.936 (dd, J=1.6, 5.2 Hz, 1 H), 8.40-8.60 (m, 1 H), 7.70-7.90 (m, 1 H), 7.40-7.60 (m, 5 H); $^{13}$CNMR (100 MHz, DMSO-d$_6$) δ186.322, 150.983, 146.113, 144.557, 135.446, 133.420, 130.750, 128.625, 128.208, 128.109, 124.802, 124.240, 123.739; MS(m/z) 292 (M+H)$^+$, 248 (M+H−CS, 100)$^+$.

DPL-004: $^{1}$H-NMR (500 MHz, CDCl$_3$) δ (ppm) 9.179 (d, J=2.0 Hz, 1 H), 8.759 (dd, J=2.0, 5.0 Hz, 1 H), 8.07 (dt, J=2.0, 8.0 Hz, 1 H), 7.35-7.48 (m, 6 H); $^{13}$CNMR (125 MHz, CDCl$_3$) δ88.837, 153.951, 148.590, 135.022(2), 134.828, 132.412, 129.917(2), 129.438(2), 126.291, 123.738; MS(m/z) 274 (M−H)$^+$, 216 (M+H−OCS, 100)$^+$.

DPL-005: $^1$H-NMR (500 MHz, CDCl$_3$): δ (ppm) 7.468 (s, 4 H), 2.713 (t, J=2.5 Hz, 2 H), 1.772 (quin, J=2.5 Hz, 2 H), 1.30-1.50 (m, 20 H), 0.948 (t, J=6.6 Hz, 3 H); $^{13}$CNMR (125 MHz, CDCl$_3$): δ198.574, 135.476, 130.264, 130.135, 130.059, 128.989, 128.519, 128.147, 44.739, 32.927, 30.673, 30.643 (2C), 30.582, 30.415, 30.355, 30.248, 29.968, 26.607, 23.694, 15.121.

DPL-006: $^1$H-NMR (400 MHz, CDCl$_3$): δ (ppm) 8.01-8.07 (m, 2 H), 7.58-7.65 (m, 1 H), 7.40-7.60 (m, 7 H); $^{13}$CNMR(100 MHz, CDCl$_3$): δ190.170, 136.632, 135.114, 134.470, 133.680, 129.545, 129.462, 129.272, 129.227, 128.764 (2 C), 127.497 (2 C), 127.337.

The above formulations could be reduced according to the actual amount of use.

Model Building

At the age of 11-12 days after birth, all suckling rats underwent a single intraperitoneal injection of sodium selenite (30 μmol/kg, i.e., 0.1 ml/10 g) for model-building. Sodium selenite solution was configured with normal saline at a concentration of 3 mM.

Animal Grouping and Dosing Protocols

At the age of 19 days after birth (D-1) of the suckling rats, 30 lens opacities were selected for a cloudy rating at Class 4 or 5; Wister suckling rats were randomly divided into 5 groups (G1-G5 groups, 6 in each group); and a cage of suckling rats as G6 was randomly selected after the animals opened their eyes (14-16 days of age). The grouping and dosing regimen in the six groups are shown in Table 1.

TABLE 1

Grouping and Administration

| Group No. | Group Name | Number of animals | Route of administration | Frequency of Administration | Dosage | Time |
|---|---|---|---|---|---|---|
| 1 | "Pirenoxine" group G1 | 6 | Conjunctival sac eye drops | 3 times/day | 10 μl/次 (0.8 mg/15 mL) | D1-D28 (D60) |
| 2 | Model groups (Placebo) G2 | 6 | Conjunctival sac eye drops | 3 times/day | 10 μl/次 (Placebo) | D1-D28 (D60) |
| 3 | New Drug G3 | 6 | Conjunctival sac eye drops | 3 times/day | 10 μl/次 (36 mg/0.1 L) | D1-D28 (D60) |
|   | New Drug G4 | 6 | Conjunctival sac eye drops | 3 times/day | 10 μl/次 (12 mg/0.1 L) | D1-D28 (D60) |
| 5 | New Drug G5 | 6 | Conjunctival sac eye drops | 3 times/day | 10 μl/次 (3.6 mg/0.1 L) | D1-D28 (D60) |
| 6 | G6 Preventive dosing group | 6 | Conjunctival sac eye drops | 3 times/day | 10 μl/次 (3.6 mg/0.1 L) | D-6-D24 (D60) |

Note:
In this experiment, the first dosing day was defined as day 1 (Day1/D1), the first day before administration was defined as (Day-1/D-1), and so on. The pH of the "pirenoxine" group was about 6.4. The pH of the subjects in the model group and the test set 1, group 2, and group 3 was 6.5. * The dosage of D1-D31 in the 1 group of samples was 36 mg/0.1 L and D32-D60 was 1.8 mg/0.1 L. G6 pH was 7.4 at D-6-D31 and 6.0 at D32-D60. The time of daily administration: the first time was 9:30 ± 30 minutes; the second time was 13 The ± 30 minutes at 30:00; the third time was 17:10 ± 30 minute.

Evaluation of Drug Efficacy on Cataract in the Rat Model

Preparation of Eye Drops Solutions

A new batch of eye drops solutions was prepared every week. Placebo was a solution that contained the same excipients but without the drug compound. The eye drops solutions were prepared as follows:
1. Sterilized water for injection was used.
2. Excipients were sodium borate, boric acid, sodium chloride, and potassium chloride.
3. An illustrative procedure: To a 250 mL volume flask were added 25 mg each of the excipients, sodium borate, boric acid, sodium chloride, and potassium chloride, an aspirin mimetic drug compound to be tested (e.g., DPL-004, 9.0 mg), and about 200 ml of sterilized water to form a mixture. The resultant mixture was shaken well to dissolve solids; and more sterilized water was added to bring the volume of solution to 250 mL, which was shaken well and then distributed into small portions. Each portion was labeled with a concentration of 3.6 mg/100 mL and the preparation date and was stored in a refrigerator for future use.
4. Eye drops solutions comprising DPL-004 at a concentration of 36 mg/100 mL and 12 mg/100 mL were prepared similarly according to the above procedure by using 90 mg and 30 mg of DPL-004, respectively, while maintaining the same amounts of excipients as shown above.

The subject suckling rats of groups G1 to G5 were treated at the age of 20 days after birth (D1), and the specific dosing information is shown in Table 1. Treatment in the G6 group was conducted after the animals opened their eyes (14-16 days old, D-6-D-4), and the specific dosing information is shown in Table 1.

At D-1, in the fourth week of treatment, the slit lamp was used at the end of administration to observe the turbidity of the lens and grade it, and the grading and scoring criteria are shown in the following Table 2.

TABLE 2

Crystal turbidity (grade 0-5)

| Rating | Characterization | Fraction |
|---|---|---|
| Level 0 | Crystal clear | 0 |
| Level 1 | Vacuoles may be seen in the peripheral or anterior cortex | 0.4 |
| Level 2 | The density of the lens nucleus is slightly increased | 1 |
| Level 3 | The lens nucleus is translucent | 2 |
| Level 4 | The lens nucleus is cloudy at least slightly transparent | 3 |
| Level 5 | The lens nucleus is cloudy to the point of being completely opaque | 4 |

TABLE 3

Body Weight (g) of Rats

| Days | | G1 | G2 | G3 | G4 | G5 | G6 |
|---|---|---|---|---|---|---|---|
| −6 | Mean | — | — | — | — | — | 35.83 |
|  | SEM | — | — | — | — | — | 0.97 |
| −1 | Mean | 43.48 | 43.88 | 45.68 | 46.10 | 45.40 | 45.27 |
|  | SEM | 2.95 | 1.32 | 3.01 | 1.92 | 1.37 | 1.35 |
| 4 | Mean | 57.07 | 54.38 | 58.22 | 59.37 | 60.25 | 62.15 |
|  | SEM | 3.98 | 1.86 | 4.22 | 2.75 | 2.28 | 1.93 |
| 11 | Mean | 96.02 | 93.75 | 97.48 | 98.03 | 101.48 | 106.70 |
|  | SEM | 6.95 | 3.68 | 7.31 | 4.53 | 4.24 | 3.61 |
| 18 | Mean | 133.87 | 134.33 | 130.98 | 138.57 | 149.00 | 140.92 |
|  | SEM | 10.74 | 7.86 | 14.02 | 5.84 | 7.22 | 7.43 |
| 25 | Mean | 163.00 | 163.63 | 161.68 | 166.05 | 188.37 | 171.78 |
|  | SEM | 17.68 | 12.84 | 19.24 | 8.39 | 11.67 | 13.25 |
| 32 | Mean | 197.18 | 196.18 | 184.12 | 188.40 | 230.95 | 211.43 |
|  | SEM | 24.50 | 17.81 | 27.12 | 12.57 | 15.38 | 7.72 |
| 39 | Mean | 219.45 | 233.73 | 210.05 | 209.05 | 257.97 | 251.03 |
|  | SEM | 30.29 | 23.95 | 31.12 | 14.10 | 17.88 | 12.20 |
| 46 | Mean | 239.75 | 262.35 | 232.55 | 232.02 | 304.65 | 283.27 |
|  | SEM | 33.80 | 30.42 | 37.71 | 15.49 | 24.76 | 16.71 |
| 53 | Mean | 255.82 | 296.10 | 256.08 | 240.18 | 323.03 | 303.65 |
|  | SEM | 38.31 | 32.38 | 41.07 | 18.05 | 31.09 | 18.00 |
| 60 | Mean | 270.00 | 295.88 | 273.13 | 269.85 | 343.05 | 330.03 |
|  | SEM | 41.99 | 38.55 | 43.91 | 18.05 | 29.49 | 22.72 |

SEM: standard error mean.

TABLE 4

Summary of lens opacity scores

| Days | | G1 | G2 | G3 | G4 | G5 | G6 |
|---|---|---|---|---|---|---|---|
| −6 | Mean | — | — | — | — | — | 4.00 |
|  | SEM | — | — | — | — | — | 0.00 |
| −1 | Mean | 4.00 | 4.00 | 4.00 | 4.00 | 4.00 | 4.00 |
|  | SEM | 0.00 | 0.00 | 0.00 | 0.00 | 0.00 | 0.00 |
| 22 | Mean | — | — | — | — | — | 4.00 |
|  | SEM | — | — | — | — | — | 0.00 |
| 28 | Mean | 3.42 | 3.67 | 3.58 | 3.50 | 3.42 | — |
|  | SEM | 0.15 | 0.14 | 0.15 | 0.15 | 0.15 | — |
| 60 | Mean | 2.92 | 3.00 | 2.75 | 2.58 | 2.58 | 3.08 |
|  | SEM | 0.29 | 0.25 | 0.22 | 0.19 | 0.23 | 0.19 |

Efficacy at D60 (G5 vs G2): (3.0-2.58) ÷ 3.0 = 14.0%; at D28: (3.67-3.42) ÷ 3.67 = 6.81%

TABLE 5

Raw data for lens opacity score

| Days | serial number | eye | G1 | G2 | G3 | G4 | G5 | G6 |
|---|---|---|---|---|---|---|---|---|
| −6 | 1 | OD | — | — | — | — | — | 4 |
|  |  | OS | — | — | — | — | — | 4 |
|  | 2 | OD | — | — | — | — | — | 4 |
|  |  | OS | — | — | — | — | — | 4 |
|  | 3 | OD | — | — | — | — | — | 4 |
|  |  | OS | — | — | — | — | — | 4 |
|  | 4 | OD | — | — | — | — | — | 4 |
|  |  | OS | — | — | — | — | — | 4 |
|  | 5 | OD | — | — | — | — | — | 4 |
|  |  | OS | — | — | — | — | — | 4 |
|  | 6 | OD | — | — | — | — | — | 4 |
|  |  | OS | — | — | — | — | — | 4 |
| −1 | 1 | OD | 4 | 4 | 4 | 4 | 4 | 4 |
|  |  | OS | 4 | 4 | 4 | 4 | 4 | 4 |
|  | 2 | OD | 4 | 4 | 4 | 4 | 4 | 4 |
|  |  | OS | 4 | 4 | 4 | 4 | 4 | 4 |
|  | 3 | OD | 4 | 4 | 4 | 4 | 4 | 4 |
|  |  | OS | 4 | 4 | 4 | 4 | 4 | 4 |
|  | 4 | OD | 4 | 4 | 4 | 4 | 4 | 4 |
|  |  | OS | 4 | 4 | 4 | 4 | 4 | 4 |
|  | 5 | OD | 4 | 4 | 4 | 4 | 4 | 4 |
|  |  | OS | 4 | 4 | 4 | 4 | 4 | 4 |
|  | 6 | OD | 4 | 4 | 4 | 4 | 4 | 4 |
|  |  | OS | 4 | 4 | 4 | 4 | 4 | 4 |
| 22 | 1 | OD | — | — | — | — | — | 4 |
|  |  | OS | — | — | — | — | — | 4 |
|  | 2 | OD | — | — | — | — | — | 4 |
|  |  | OS | — | — | — | — | — | 4 |
|  | 3 | OD | — | — | — | — | — | 4 |
|  |  | OS | — | — | — | — | — | 4 |
|  | 4 | OD | — | — | — | — | — | 4 |
|  |  | OS | — | — | — | — | — | 4 |
|  | 5 | OD | — | — | — | — | — | 4 |
|  |  | OS | — | — | — | — | — | 4 |
|  | 6 | OD | — | — | — | — | — | 4 |
|  |  | OS | — | — | — | — | — | 4 |
| 28 | 1 | OD | 3 | 3 | 3 | 3 | 4 | — |
|  |  | OS | 3 | 3 | 3 | 3 | 4 | — |
|  | 2 | OD | 4 | 4 | 4 | 4 | 3 | — |
|  |  | OS | 4 | 4 | 4 | 4 | 3 | — |
|  | 3 | OD | 4 | 4 | 3 | 3 | 3 | — |
|  |  | OS | 4 | 4 | 3 | 3 | 3 | — |
|  | 4 | OD | 4 | 4 | 4 | 4 | 4 | — |
|  |  | OS | 3 | 4 | 4 | 4 | 4 | — |
|  | 5 | OD | 3 | 4 | 4 | 4 | 3 | — |
|  |  | OS | 3 | 4 | 4 | 4 | 3 | — |
|  | 6 | OD | 3 | 3 | 4 | 3 | 4 | — |
|  |  | OS | 3 | 3 | 3 | 3 | 3 | — |
| 60 | 1 | OD | 2 | 2 | 2 | 2 | 3 | 4 |
|  |  | OS | 2 | 2 | 2 | 2 | 4 | 3 |
| 60 | 2 | OD | 4 | 4 | 3 | 3 | 2 | 3 |
|  |  | OS | 4 | 4 | 3 | 3 | 2 | 2 |
| 60 | 3 | OD | 4 | 4 | 2 | 2 | 2 | 4 |
|  |  | OS | 4 | 3 | 2 | 2 | 2 | 3 |
| 60 | 4 | OD | 4 | 3 | 4 | 4 | 3 | 2 |
|  |  | OS | 3 | 3 | 4 | 3 | 4 | 4 |
| 60 | 5 | OD | 2 | 4 | 3 | 3 | 2 | 3 |
|  |  | OS | 2 | 3 | 3 | 3 | 2 | 3 |
| 60 | 6 | OD | 2 | 2 | 3 | 2 | 2 | 3 |
|  |  | OS | 2 | 2 | 2 | 2 | 3 | 3 |

OD: right eye; OS: left eye.

General Clinical Observations

The DPL-004 groups with different concentrations were compared with the placebo group and the pirenoxine group, no abnormal symptoms (including activity status, body weight, skin hair, secretion morphology and color, etc.) were seen in any group.

Conclusions

Preliminary screening with efficacy tests of the new drug candidate compound DPL-004, 2-[(pyridine-3-carbonyl)sulfanyl]benzene-1-carbothioic S-acid, with several different concentration groups and placebo group (G2) and "pirenoxine" group (G1), were carried out in a period of 60 days (66 day administration in the G6 early intervention group) on a Wistar rat cataract model induced by sodium selenite, with a frequency of 3 times/day and 10 μL of eye drop each time. The efficacy of new drug compound was evaluated by quantifying the lens turbidity score. The lens opacity score was 4.0 for all enrolled rats. Findings and conclusions are as follows:

1. The new drug groups compared with the placebo group showed some efficacy. In particular, the efficacy of compound DPL-004 on the G5 group of rats was among the highest at all detection stages, the performance was stable, and the compound DPL-004 improved the opacity score over time in comparison with the placebo (e.g., efficacy by 6.81% at D28 and by 14.0% at D60). More notably, DPL-004 showed an effect of gradually reversing cataracts.

2. The correlation between the concentration and the efficacy of DPL-004 has been preliminarily established. At D60, the efficacy of G4 and G5 groups was the same at 14.0%, which related to new drug concentrations of 12 mg/0.1 L and 3.6 mg/0.1 L, respectively. At D28, the efficacy of G4 and G5 was 4.63% and 6.81%, respectively.

3. The efficacy of weakly acidic eye drops is significantly better than that of weakly alkaline. This finding is original and has not been reported in literature. The drug concentration of G5 is the same as that of G6 (early intervention group), in the period of 28 days, with the lens opacity score of 3.42 (the efficacy was 6.81%) and 4.0 (3.67 in the placebo group); the only difference was in pH, 6.5 and 7.4 respectively. When adjusting its pH from 7.4 to 6.0, the G6 group at D60 (pH 6.0 for 28 days) showed the lens turbidity score reduced from 4.0 (pH 7.4 for 28 days) to 3.08; , the largest single-month decline. Later development will be optimized between pH 6.0-6.5.

4. Safety of new drug compound (DPL-004): during the observation of the 60-day administration phase, the new drug groups with different concentrations compared with the placebo group and the "pirenoxine" group, no abnormal symptoms were seen from the active state, body weight, skin hair, the form and color of the discharge.

It will be understood by those of skill in the art that the various embodiments and examples of the present disclosure are illustrative only and are not intended to limit the scope of the present disclosure, and numerous modifications can be made without departing from the spirit and scope of the invention disclosed and are intended to be encompassed by the present disclosure.

What is claimed is:

1. An active pharmaceutical ingredient (API) selected from:

DPL-003

DPL-004

DPL-005

DPL-006 or a pharmaceutically acceptable salt thereof.

2. An eye drops solution comprising a compound of claim 1, a pharmaceutically acceptable carrier, and optionally one or more pharmaceutical excipients.

3. The eye drops solution of claim 2, wherein the pharmaceutically acceptable carrier is water, and wherein the eye drops solution further comprises a pharmaceutical excipient selected from sodium chloride, potassium chloride, boric acid, sodium borate, benzalkonium chloride, glycol, glycerin, polysorbate, carboxy methylcellulose sodium, and combinations thereof.

4. The eye drops solution of claim 2, wherein concentration of the API in the eye drops solution is in a range from 0.01 mg/mL to 0.05 mg/mL.

5. The eye drops solution of claim 2, wherein the concentration of the API is in a range from 0.018 mg/mL to 0.036 mg/mL.

6. The eye drops solution of claim 2, having a pH in the range from 5.5 to 8.5, inclusive.

7. The eye drops solution of claim 6, wherein pH is adjusted using an acid selected from hydrochloric acid, sulfuric acid, phosphoric acid, acetic acid, and combinations thereof.

8. A method of treating an age-related cataract in an eye of a subject, comprising administering to the eye of the subject a therapeutically effective amount of the eye drops solution of claim 2.

9. The method of claim 4, wherein the subject is a human, or a mammalian animal selected from dogs (canine), cats, rabbits, horses, ox, hamster.

10. The method of claim 8, wherein dose range of API in the eye drops solution administered to the subject is from 10 μL to 120 μL each time, or from 0.00073 mg/kg body weight to 0.015 mg/kg body weight, or from 2.5 nmol/kg body weight to 50 nmol/kg body weight.

11. The method of claim 8, wherein the eye drops solution is administered to the subject in a frequency from one time daily to 5 times daily.

* * * * *